(12) United States Patent  
Sobue et al.

(10) Patent No.: US 7,243,893 B2  
(45) Date of Patent: Jul. 17, 2007

(54) DIALYSIS SOLUTION BAG STAND

(75) Inventors: Katsuyoshi Sobue, Ome (JP); Toshihisa Kudo, Machida (JP); Yoritate Okada, Yokohama (JP); Takayuki Miyanishi, Ichikawa (JP); Hiroshi Oishi, Kokubunji (JP)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 133 days.

(21) Appl. No.: 10/740,934

(22) Filed: Dec. 18, 2003

(65) Prior Publication Data

US 2005/0133674 A1 Jun. 23, 2005

(51) Int. Cl.
*A47B 97/04* (2006.01)
(52) U.S. Cl. ..................... 248/459; 248/460
(58) Field of Classification Search .......... 248/454, 248/455, 459, 460, 95; 604/80, 322
See application file for complete search history.

(56) References Cited

U.S. PATENT DOCUMENTS

| 2,726,835 | A |   | 12/1955 | Hummel |
| 4,496,354 | A | * | 1/1985 | Steer et al. .................. 604/322 |
| D304,239 | S | * | 10/1989 | Miller ......................... D24/128 |
| 5,413,305 | A | * | 5/1995 | Leeb ............................ 248/460 |
| 5,474,683 | A | * | 12/1995 | Bryant et al. ............... 210/646 |
| 5,480,118 | A | * | 1/1996 | Cross .......................... 248/459 |
| 6,117,122 | A |   | 9/2000 | Din |
| 6,270,049 | B1 | * | 8/2001 | Olvey ...................... 248/441.1 |
| 6,277,815 | B1 |   | 8/2001 | Knerr |
| 6,423,041 | B1 | * | 7/2002 | Grant .......................... 604/322 |
| 6,447,492 | B1 | * | 9/2002 | Frohn .......................... 604/322 |
| 6,645,191 | B1 |   | 11/2003 | Knerr |

FOREIGN PATENT DOCUMENTS

FR 2786729 A 6/2000

* cited by examiner

*Primary Examiner*—Amy J. Sterling
(74) *Attorney, Agent, or Firm*—Joseph P. Reagen; Bell, Boyd & Lloyd LLC

(57) ABSTRACT

A stand for a medical fluid treatment, a system for supporting multi-chamber medical fluid bags and a method for testing whether the multi-chamber bags have been preset properly for therapy are provided. In one embodiment a multi-section stand is provided that is folded in a number of places to produce a structure upon which fluid from a properly preset solution bag flows readily to a patient, but upon which a dual-chamber bag that has not been modified properly for treatment collapses, folds or falls to a position providing visual indication that the chamber seal needs to be released or opened.

12 Claims, 4 Drawing Sheets

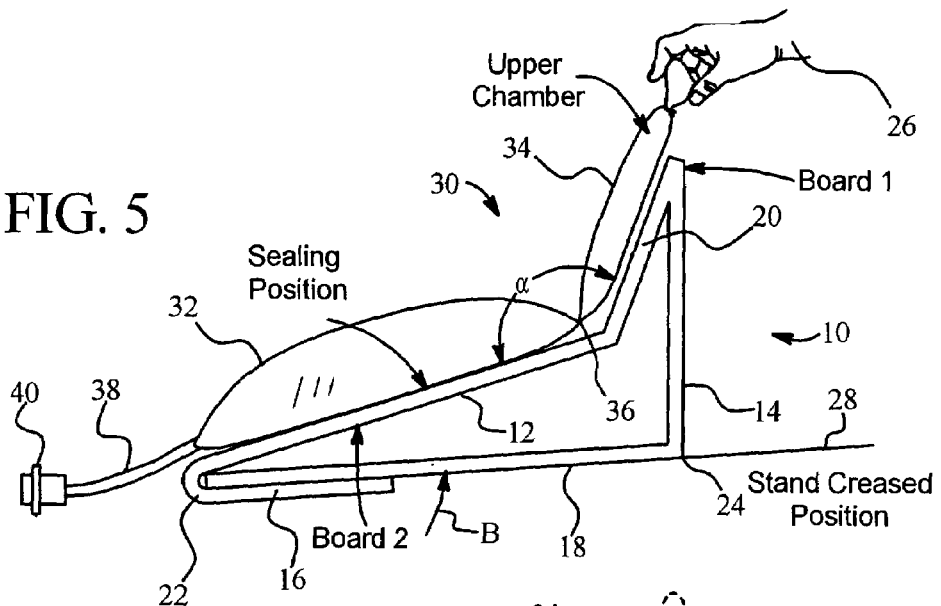
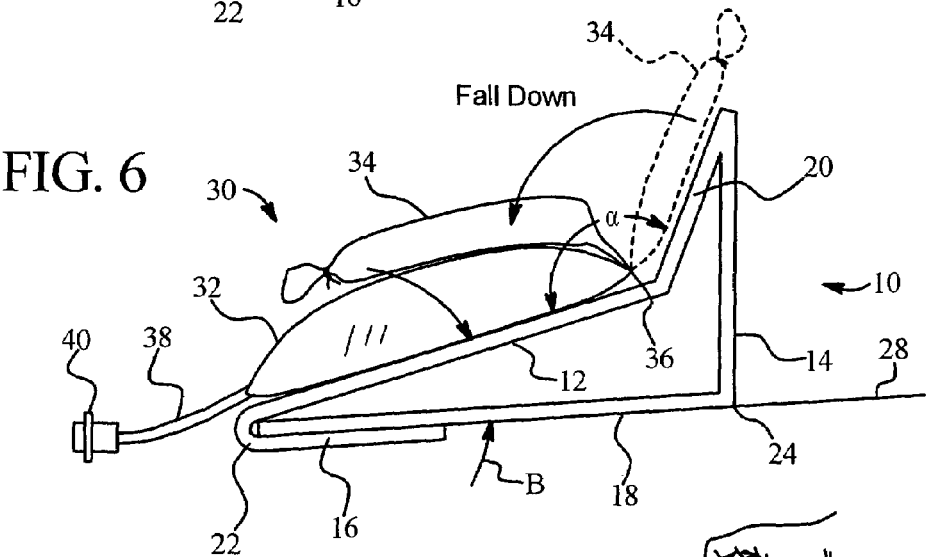
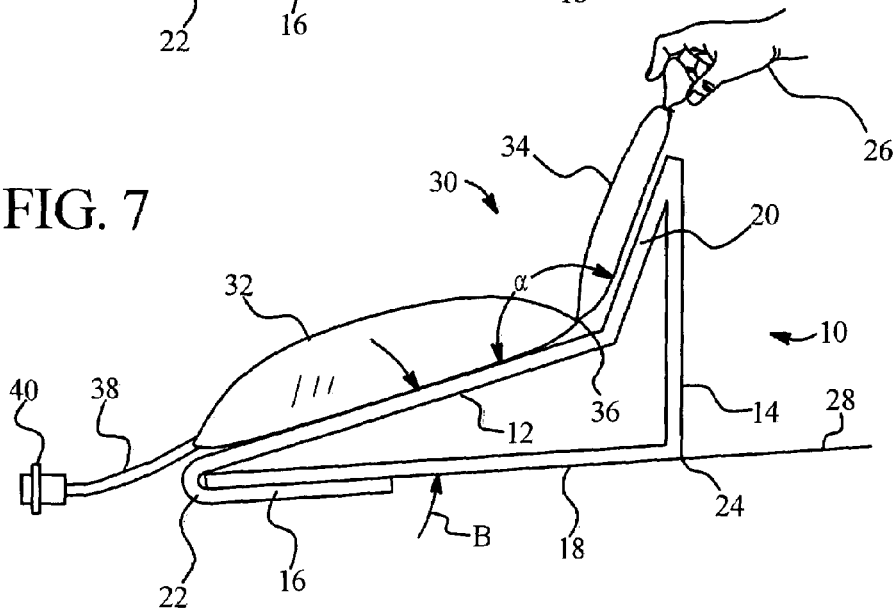

DIALYSIS SOLUTION BAG STAND

BACKGROUND OF THE INVENTION

The present invention generally relates to dialysis systems. More specifically, the present invention relates to an apparatus and method for coordinating and testing multiple dialysis fluid chamber bags.

Due to disease, injury or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life sustaining. One who has failed kidneys could not continue to live without replacing at least the filtration functions of the kidneys.

Hemodialysis and peritoneal dialysis are two types of dialysis therapies commonly used to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about 120 liters, is used to dialyze the blood during a single hemodialysis therapy. The spent dialysate is then discarded. Hemodialysis treatment lasts several hours and is generally performed in a treatment center about three or four times per week.

Peritoneal dialysis utilizes a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD"), automated peritoneal dialysis and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. Manual peritoneal dialysis performed by the patient requires a significant amount of time and effort from the patient.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines are fluidly connected to a catheter implanted in the patient. The APD machines are also fluidly connected to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. APD frees the patient from having to manually performing the drain, dwell, and fill steps.

For each of the above-described dialysis therapies, each of the associated cycles typically consumes a separate bag of solution or dialysate. Over the course of therapy, multiple bags of such solution are used. In many instances, solution bags with a single chamber or pouch are used. In such a case, the solution is completely premixed, sterilized and ready to use. In other instances, the bags include multiple chambers that divide a base solution from an additive. With multi-chamber bags, the patient must break a seal to enable the additive to run to the base solution. It happens sometimes that the patient does not properly open the seal or forgets to open the seal completely. In such a case, therapy does not take place properly.

It is therefore desirable to have a ready apparatus to organize and support multiple solutions bags sequentially or simultaneously.

It is also desirable to have an apparatus that ensures that the patient has properly preset or opened a multi-chamber bag for use.

SUMMARY OF THE INVENTION

The present invention includes an apparatus and method for holding or supporting medical fluid therapy supply bags and for ensuring that if a multiple or dual chamber supply bag is used, that the bag has been properly preset for therapy. Multiple chamber or dual chamber supply bags are known and popular medical fluid supply devices. The bags house different components of an overall solution that is delivered to a patient for therapy. For example, a dual chamber dialysis fluid or dialysate bag can include one chamber with sterile fluid, such as sterile water with electrolytes, wherein a separate chamber includes an additive such as dextrose. The components are stored separately until time of use. At that time the patient or caregiver is required to break a seal, such as the Easy to Peal Seal™ of dual chamber bags provided by the assignee of the present invention. It is important that such opening of the seal is preformed prior to therapy. The present invention provides not only a stand that supports the supply bags at an angle suitable for delivering the overall solution throughout therapy, the stand also provides an apparatus and method for visually indicating to the patient or caregiver whether the seal has been opened properly or not.

In one aspect of the present invention, a supply bag stand is provided that has a seat portion and a back portion. The seat portion and back portion are positioned at an angle with respect to one another. That angle is well-suited for enabling medical fluid, such as dialysate, to flow from the bag to the medical fluid apparatus, such as an APD machine. The angle is also set so that if the seal between two chambers of a multi-chamber bag has not been properly opened, a chamber that has been propped or positioned up against the back of the stand falls over onto a chamber that has been set onto the seat portion of the stand. That action provides a readily seen visual cue that the solution bag is not properly preset for therapy. On the other hand, if the seal between the dual chambers has been opened properly, the bag remains in position, so that the first chamber remains propped or positioned against the back portion, while the other chamber remains situated on the seat portion, enabling the properly mixed solution to flow to the patient.

In one embodiment, the chamber that rests on the seat portion of the stand has an outlet tube or stem that connects fluidly to the medical fluid therapy apparatus. The present invention is expressly not limited to dialysis systems. The present invention is however well-suited for renal failure therapy treatment as well as congestive heart failure treatment. The medical fluid apparatus can therefore be a CAPD apparatus APD apparatus, hemofiltration apparatus, hemodiafiltration apparatus or any combination thereof.

It is contemplated to provide the stand in a number of different ways using different components. One preferred apparatus includes a series of sections or boards that are hinged sequentially together. In particular, in one embodiment the stand includes two inner boards and two outer boards, wherein the outer boards are hingedly connected to the inner boards. The inner boards are then separated by a middle portion, which can be flexible, semi-flexible, semi-rigid or rigid. To create a stand, the sections or boards are folded to create a sturdy structure with the back portion set at an angle with respect to the seat portion. The back portion includes the middle portion separating the inner sections. The patient or caregiver sets the multi-chamber solution bag on the stand constructed from the multiple folded sections described above, so that one bag rests on the seat portion, while the other bag rests on the middle, e.g., flexible portion of the back. That flexible portion is movable so that if the seal between the chambers of the bag is not broken, fluid in the upper section is pulled downward by gravity, causing the upper chamber to fall down onto the lower chamber.

The foldable boards or rigid sections are plastic, metal, wood or composite structures that are coated in one embodiment with a flexible water impermeable coating, such as a thin plastic coating. The plastic coating also creates hinge seams between the inner and outer sections as well as between the middle portion and the inner boards. Such material and configuration are cost effective, light weight, sturdy, easy to clean and safe.

In another embodiment, two rigid pieces are hinged together, such that the back portion folds away from the seat portion to create the desired angle between the two members. The seat portion is also angled slightly relative to a horizontal plane, so that fluid flows properly out of the supply bag to the patient. This alternative embodiment may or may not use a flexible backing section or piece described above for the folded embodiment. Nevertheless, the angle created between the two members in this alternative embodiment is sufficient so that if the seal is not properly opened, the upper fluid chamber falls down onto the lower fluid chamber and thereby provides visual indication that the bag is not properly preset for therapy. If, however, the seal has been opened, the angle of the alternative apparatus allows the fluid from the upper chamber to flow through the lower chamber, combining with the fluid in same to create an overall mixture that is delivered to the patient. The alternative stand is likewise made of one or more materials selected from the group consisting of plastic, metal, wood, a composite material and any combination thereof.

In any of the embodiments described herein, the stand can be sized to hold a single solution bag or multiple solution bags. If the stand is sized to hold multiple solution bags, each of those bags can be tested sequentially or simultaneously to ensure that the seal separating dual or multiple chambers is opened properly prior to therapy. Additionally, if the solution bags have not been properly preset for therapy, the stand supporting the multiple solution bags provides visual indication of same, for one or more or all of the supply bags. If the bags have been properly preset for therapy, the stand enables fluid to flow as designed through the multipe chambers of each multi-chamber bag.

It is therefore an advantage of the present invention to provide a supply bag medical stand that enables fluid from a bag set thereon to flow properly to a medical fluid therapy device.

It is also an advantage of the present invention to provide a supply bag stand that is operable with multiple renal failure therapy apparatuses, such as a CAPD apparatus, APD apparatus, hemodialysis apparatus, hemofiltration apparatus, hemodiafiltration apparatus and any combination thereof.

It is a further advantage of the present invention to provide a stand that indicates when one or more bags set thereon has not been properly preset for therapy.

Further still, it is an advantage of the present invention to provide a stand operable so that when one or more solution bags set thereon has not been properly opened to allow fluid to flow from one chamber to another, such failure is visually indicated.

Moreover, it is an advantage of the present invention to provide a medical fluid supply bag stand that enables fluid to: (i) flow properly from one chamber through another chamber; (ii) mix with fluid in the other chamber; and (iii) flow as a mixed fluid properly to the patient.

Still further, it is an advantage of the present invention to provide a lightweight, compact, safe, water impermeable, sturdy and cost effective medical fluid supply bag stand.

Yet another advantage of the present invention is to provide a medical fluid supply bag stand that is readily assembled and disassembled.

Additional features and advantages of the present invention are described in, and will be apparent from, the following Detailed Description of the Invention and the figures.

BRIEF DESCRIPTION OF THE FIGURES

FIGS. 5 and 6 illustrate the stand test method and visual indication provided when the multiple chamber solution bag has not been opened properly.

FIGS. 7 and 8 illustrate the stand test method and the flow of fluid from one chamber to another and from the dual chambers to the patient when the multiple chamber bag has been properly preset for therapy.

DETAILED DESCRIPTION OF THE INVENTION

The present invention includes an apparatus and method for supporting one or more medical fluid supply bag during treatment as well as testing such bags to determine whether a seal or flow restriction has been opened to allow fluids from one chamber to enter a second chamber to thereafter provide a ready therapy fluid for treatment. The stand and method of testing described herein apply to any medical fluid treatment using supply bags having multiple chambers, wherein fluids or constituents within the chambers are mixed at the time of therapy. In particular, the stand and test method are well suited for renal failure or congestive heart failure treatment. For example, the stand and test method are well suited for CAPD, APD, hemodialysis, hemofiltration, hemodiofiltration and any combination thereof.

Figure 1:
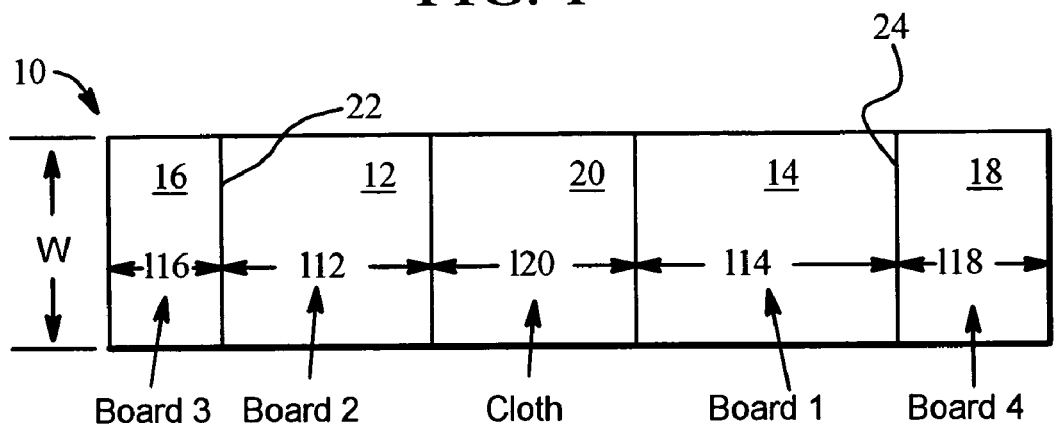
FIG. 1 illustrates one embodiment of the stand of the present invention shown in the flat, with multiple foldable sections.

Referring now to the drawings and in particular to FIGS. 1 to 4, one embodiment of the supply bag stand of the present invention is illustrated by stand 10. Stand 10 is shown in various stages of formation in FIGS. 1 to 4. FIG. 1 illustrates stand 10 flattened out and before the stand is folded. As illustrated, stand 10 includes two inner sections or boards 12 and 14 and two outer sections or outer boards 16 and 18. Sections or boards 12 to 18 are relatively rigid. A flexible, sheet-like or cloth-like central section 20 is provided between inner sections 12 and 14. In alternative embodiments, central section 20 is semi-flexible, semi-rigid or rigid. Outer section 16 and inner section 12 are separated by hinge seam 22. Inner section 14 and outer section 18 are separated by hinge seam 24. Hinge seams 22 and 24 enable outer sections 16 and 18 to rotate in either direction relative to inner sections 12 and 14. Thus outer sections 16 and 18 can be folded in either direction and to any suitable angle relative to inner sections 12 and 14, respectively.

Inner sections 12 and 14 can both in turn rotate or bend in either direction and to any suitable angle with respect to central flexible, semi-rigid or rigid portion 20. It should be appreciated therefore that relatively rigid sections 16, 12, 14 and 18 and the, e.g., flexible, central portion 20 can be bent in a myriad of combinations of ways.

The relatively rigid portions 12, 14, 16, and 18 in one embodiment include semi-rigid or rigid pieces that are covered with and connected by a thin coating. In one embodiment, the inside semi-rigid or rigid structures are made of plastic, pasteboard, wood, metal, a composite material and any combination thereof. The thin outer coating in one embodiment is a strong, water resistant and easily cleaned polymer material, such as vinyl. Alternatively, the outer coating is soft cloth, a woven material or other strong and water resistant or impermeable fabric or material. The outer coating material is also crimped, heat sealed or otherwise bonded together to form the hinge seams 22 and 24. Similar seals, crimps or other type of connections are also made along the inside edges of inner sections 12 and 14 to separate same from central portion 20. Central portion 20 can be comprised of one or more plies of the outer coating or include alternatively a semi-flexible, semi-rigid or rigid inside structure, such as that used for portions 12, 14, 16 and 18.

As seen in FIG. 1, sections 12 through 20 each have the same or substantially same width w in one embodiment. Width w can be varied to support one or a plurality of supply bags. Such support is shown in detail below. FIG. 1 also shows that the sections 12 to 20 have varying lengths $l_{12}$ to $l_{20}$. Lengths $l_{12}$ to $l_{20}$ are set so that when corresponding sections 12 to 20 are bent to form stand 10, the proper or desired structure having the sections set at the desired angles is formed.

Figure 2:
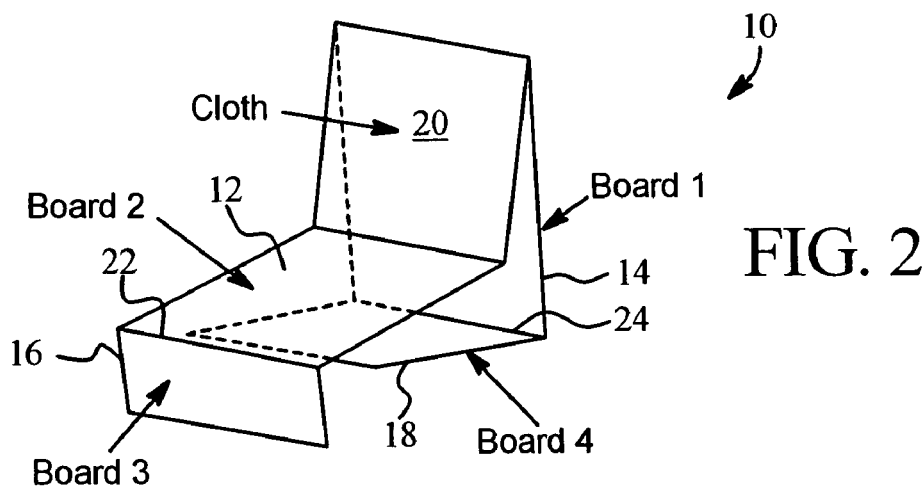
FIG. 2 illustrates the stand of FIG. 1 at one point in the assembly thereof.
Figure 3:
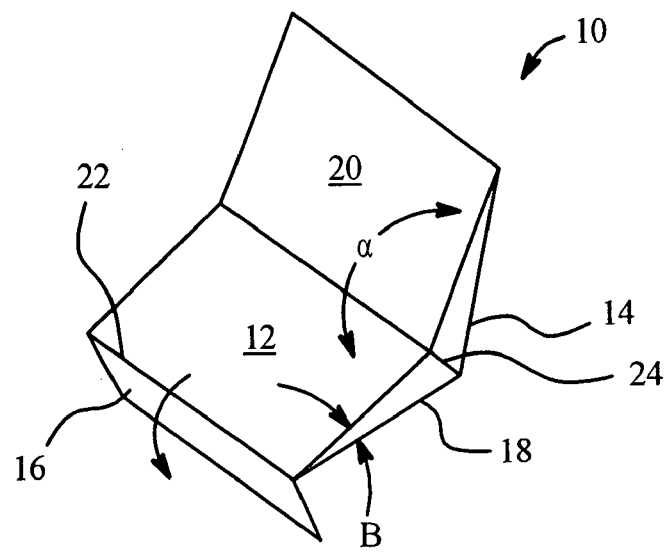
FIG. 3 illustrates the stand of FIG. 1 in a second point in the assembly thereof.

Referring now to FIGS. 2 and 3, stand 10, shown in partially bent forms, illustrates how the stand is formed from the flat shown in FIG. 1. FIGS. 2 and 3 show that inner section 12 and outer sections 16 and 18 are bent to form a base or seat portion of stand 10, while flexible central portion 20 and inner section 14 are bent to form the back or side portion of stand 10. In an alternative embodiment, portion 20 and inner section 14 are adhered or otherwise fastened together. As seen in FIGS. 2 and 3, outer section 16 is bent downward from inner section 12 around the end of outer section 18, which is bent towards seam 22 with respect to inner portion 14. Outer portion 18 is bent as illustrated along hinge seam 24.

In one embodiment, the weight of rigid boards 12, 14, 16 and 18 as well as the flexible portion 20 is enough to hold the structure in place. Alternatively, fasteners such as snaps, Velcro™ fasteners, tabs and/or slits are provided on outer portions 16 and 18 to hold the finished structure shown in FIG. 4 in place. Section 18 abutted against hinge seam 22 between sections 12 and 16 and the lengths $l_{12}$, $l_{14}$ and $l_{20}$ collectively cause board 14 to be positioned at least somewhat vertically, so that board 14 and central portion 20 form a back or side wall at an angle α shown in FIGS. 2 through 4.

Figure 4:
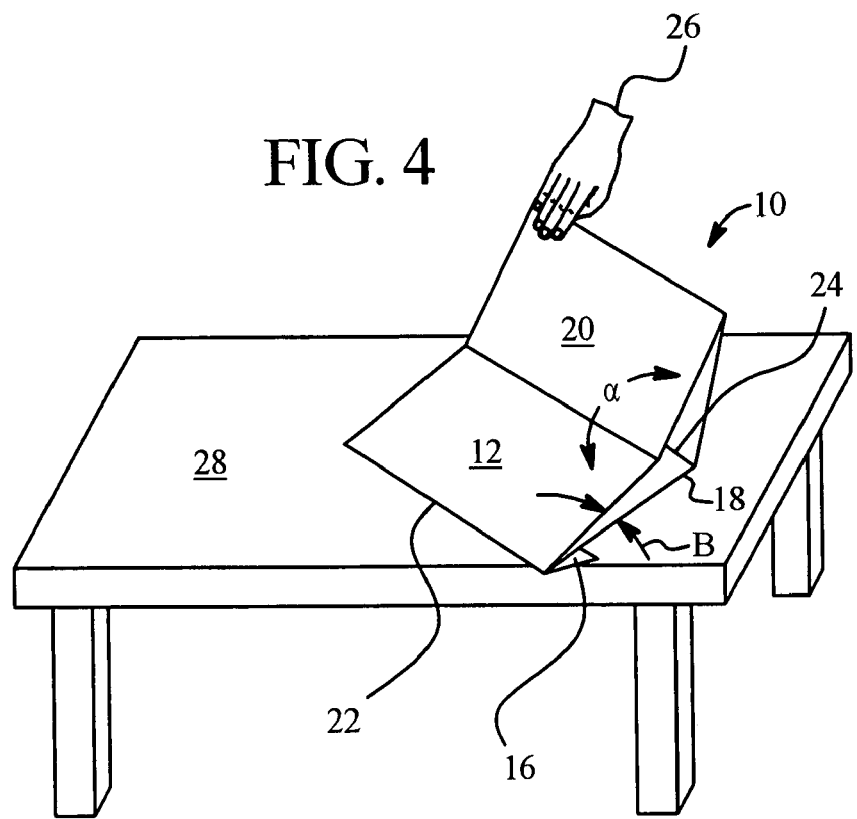
FIG. 4 illustrates the assembled stand of FIG. 1 placed on a horizontal surface.

FIG. 4 shows that the completed structure 10 is placed by a person 26 onto a horizontal surface 28, such as a table, night stand, floor or other substantially horizontal structure. Once the formed stand 10 is placed onto the flat surface 28, the stand is ready for use. It should be appreciated that not only does angle α exist between inner section 12 and central flexible portion 20, a second angle β is formed between inner section 12 and outer section 18. As seen in FIG. 4, outer section 18 and mating section 16 are substantially parallel to and indeed lay on top of horizontal surface 28. Angle β is provided so that when one or more solution bag is properly preset, e.g., the seal of the dual chamber bag is opened, the fluid flows from the bag due to the slight downward grade of inner section 12 from angle β towards the horizontal surface 28.

Referring now to FIGS. 5 to 8, one embodiment for performing the supply bag test procedure of the present invention is illustrated using stand 10 as previously described. FIGS. 5 to 8 each illustrate a multi-chamber or dual chamber bag 30. Bag 30 includes lower chamber 32 and upper chamber 34, which are separated via a seal or removable partition 36. In one embodiment, lower chamber 32 holds the main supply of medical fluid and upper chamber 34 holds an additive, which for any suitable purpose is advantageously kept separate from the main fluid in chamber 32 until use. To that end, multiple additive chambers, such as chamber 34 can be provided, wherein each such chamber holds a separate additive, which is advantageously kept separate from the main fluid within chamber 32 and from the other additives in other additive chambers 34. It should be appreciated however that dual chamber or multi-chamber supply bag 30 in an alternative embodiment is configured so that the main portion or base solution is kept in upper chamber 34, while an additive is kept in lower chamber 32.

In one preferred embodiment, dual chamber bag 30 holds the components of a dialysis solution or dialysate, which is used for peritoneal dialysis, hemodialysis, hemofiltration or hemodiafiltration. In such a case, lower chamber 32 can hold the base liquid portion of the dialysate, which is largely sterile water plus electrolytes, such as potassium, calcium, sodium, chloride and the like. Upper chamber 34 holds an additive, such as dextrose, one or more of the above electrolytes, an NaCI powder or concentrate and the like, which is advantageously kept separate from the base fluid in chamber 32. Chamber 34 can alternatively hold any desirable type of additive, which can be in solid particle form, liquid form, concentrate form or any other form in which material can flow from chamber 34 to chamber 32 due at least in part to the force of gravity.

FIGS. 5 and 6 illustrate the test sequence in which seal 36 has not been opened or has not been opened properly. In FIG. 5, patient or operator 26 places bag 30 on stand 10 as illustrated so that lower chamber 32 sets and rests on inner section 12 of stand 10, while upper chamber 34 sets or rests on central, e.g., flexible, portion 20. In an embodiment, section 12 and portion 20 will both move slightly due to the weight of the liquid inside lower chamber 32 and upper chamber 34. Relatively rigid section 12 will pivot slightly about hinge seam 22 and may also flex or bow slightly in the middle. Flexible portion 20 may also pivot slightly about the seam connecting portion 20 to inner portion 14. The flexible material will also move to conform with the movement of fluid inside upper chamber 34. The angle α between inner rigid section 12 and flexible section 20 may also change slightly.

FIG. 6 illustrates that angle α and the angle of inner portion 14 with respect to the horizontal surface 28 are preset via the formation of stand 10 so that if seal 36 is not opened or not opened properly, the weight of fluid within upper chamber 34 causes the upper chamber to fall forward or tip about the axis of seal 36 onto lower chamber 32. Such action is a distinct visual cue that is likely to be noticed by patient or operator 26. Indeed, because the patient or operator must connect connector 40 located at the end of stem 38 to the medical fluid apparatus, it would be highly unlikely that the patient or operator would not notice the upper chamber 34 laying on lower chamber 32. Therefore, the configuration of stand 10 provides an effective visual test and tool for the patient or operator to ensure that the multi-chamber or dual chamber bag 30 is properly preset before therapy.

Figure 8:
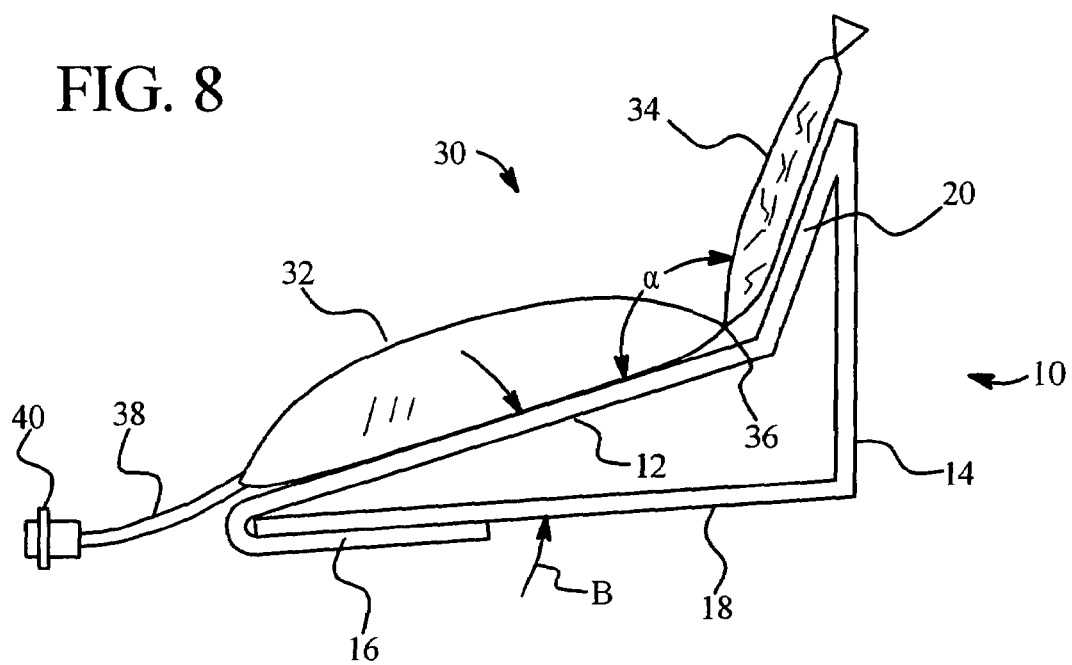

FIGS. 7 and 8 illustrate the test outcome when seal 36 has been opened properly. In such a case, fluid such as additive fluid, flows from upper chamber 34, through the opened seal 36, into lower chamber 32 and mixes with the fluid therein. Thereafter, the properly mixed fluid, such as dialysis fluid, flows through stem 38 and connector 40 to the medical fluid therapy apparatus. As discussed above, the angle β between inner section 12 and outer section 18/surface 28 enables the fluids mixed from chamber 34 and chamber 32 to flow smoothly out of stem 38, connector 40 into the medical fluid therapy device.

Since the fluid in FIGS. 7 and 8 is able to flow from upper chamber 34 to lower chamber 32, the weight of fluid in upper chamber 34 does not cause the upper chamber to fall or fold over onto lower chamber 32. Instead, upper chamber 34 is seen to shrink or decrease in fluid volume. When seal 36 is properly opened, stand 10 operates to hold chambers 32 and 34 of bag 30 in place properly throughout therapy. After therapy, stand 10 is folded conveniently into a flat structure that is easily stored and consumes little space. Stand 10 in at least certain embodiments is also collapsible, allowing energy from a collision, for example by a running or falling child, to be absorbed through such collapse, reducing the likelihood of harm or injury from the collision.

As discussed above, stand 10 may have a width w so that multiple dual chamber bags 30 can be placed thereon. The test provided by stand 10 would therefore be performed on each of the multiple chamber bags 30. That is, any multi-chamber bag on stand 10 that is not properly opened or preset for therapy, fails the test as seen when its upper chamber 34 falls onto its lower chamber 32. It should therefore be appreciated that the test provided by stand 10 of the present invention can test a plurality of multi-chamber bags at once.

Stand 10 in one embodiment also displays graphical and/or textual instructions to: (i) fold stand 10 properly; and (ii) explain the dual or multi-bag test procedure. Those same instructions can be provided on bag 30 for operation with stand 10.

Figure 9:
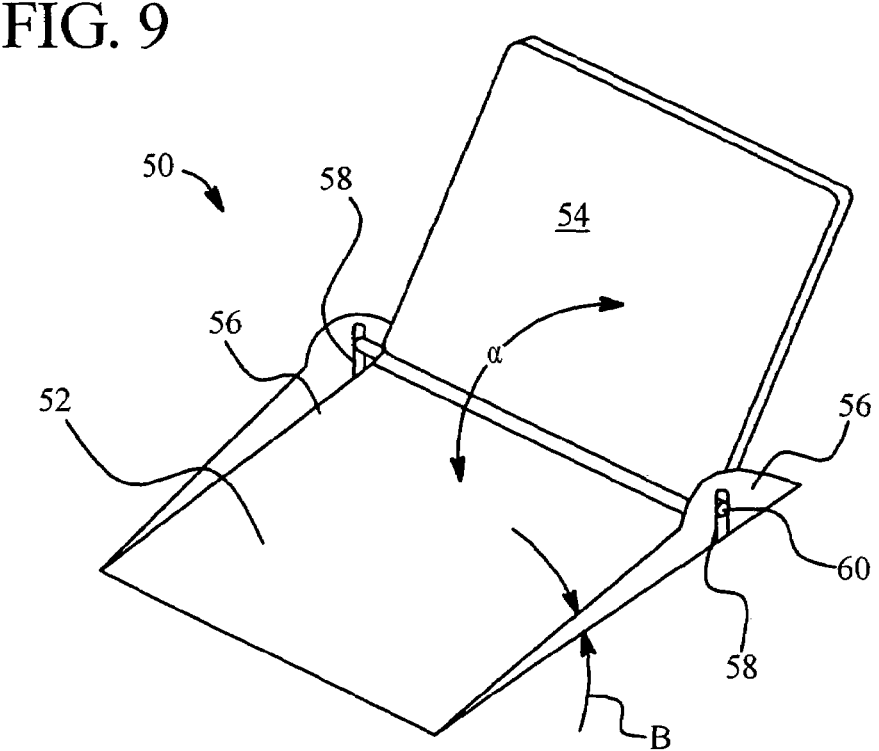
FIG. 9 illustrates an alternative embodiment of the stand apparatus of the present invention.

FIG. 9 illustrates an alterative embodiment for the stand of the present invention. Alternative stand 50 includes a seat portion 52 and a back or rear portion 54. In one embodiment, both seat 52 and back 54 are single pieces of formed plastic, paste board, metal, composite material or any combination thereof. Seat 52 and back 54 can also have a thin water impermeable coating, such as a plastic, e.g., vinyl, coating.

As illustrated in FIG. 9, seat 52 is angled at angle β with respect to the horizontal surface on which stand 50 is placed. In use, back 54 is rotated up from seat 52 to the desired angle α for performing the test described above. Stand 50: (i) enables proper flow; (ii) tests one or more multi-chamber solution bags; and (iii) performs each of the functions described above for stand 10. That is, angles α and β are selected so that the weight of additive or fluid in an upper chamber causes the upper chamber to tip over onto lower chamber if the seal between chambers is not opened properly.

In the illustrated embodiment, seat 52 defines or includes sides 56. Sides 56 each define an aperture 58. A hinge pin or hinge device 60 is inserted through aperture 58 to a mating aperture defined by back 54. Back 54 is thereby hingedly connected to side 56 and seat 52. A stop, not illustrated, can be provided so that seat 54 is opened automatically to the desired angle α. That stop in one embodiment is adjustable to fine tune the setting of angle α.

It should be appreciated that those of skill in the art can develop other methods and apparatuses for hingedly connecting back 54 to seat 52. For example, it is possible to place a plurality of detents on sides 56 so that back 54 can be rotated and held at multiple angles for angle α. In any case, when stand 50 is not in use, back 54 folds conveniently into seat 52 and stand 50 is readily stored away as a flat item. Stand 50 can also be provided with suitable instructional graphics and/or indicia.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A medical fluid supply bag system comprising:
   at least one medical fluid supply bag;
   a stand including two members angled with respect to one another, the members positioned and arranged to support the at least one medical fluid supply bag at an angle suitable to dispense medical fluid for therapy;
   wherein the bag includes a plurality of chambers and a seal between at least two of the chambers; and
   wherein the angle is set at less than ninety degrees to cause the bag to (i) act in a first manner if the seal between the two chambers has been opened properly for therapy and (ii) to act in a second manner if the seal has not been opened properly for therapy.

2. The medical fluid supply bag system of claim 1, wherein the members are foldably engaged with respect to each other and folded/unfolded to form the angle.

3. The medical fluid supply bag system of claim 1, wherein the members are hinged with respect to each other and rotated about the hinge to form the angle.

4. The medical fluid supply bag system of claim 1, wherein one of the members is a seat member that is relatively rigid, while the other member is a back member that is relatively flexible.

5. The medical fluid supply bag system of claim 4, wherein flexible back member is supported by a third member, the third member being relatively rigid.

6. The medical fluid supply bag system of claim 1, wherein the members of the stand include a flexible water impermeable cover.

7. The medical fluid supply bag system of claim 1, wherein the supply bag includes a stem extending therefrom that connects fluidly to a dialysis apparatus.

8. The medical fluid supply bag system of claim 1, wherein the supply bag is connected to a dialysis apparatus selected from the group consisting of: a continuous ambulatory peritoneal dialysis apparatus, an automated peritoneal dialysis apparatus, a hemodialysis apparatus, a hemofiltration apparatus, a hemodiaflitration apparatus and any combination thereof.

9. A medical fluid supply bag stand comprising:
   first and second inner boards and first and second outer boards, the first and second inner boards connected hingedly and respectively to the first and second outer boards, the first and second inner boards separated by and connected moveably to a middle portion;
   wherein the boards are folded together to form a structure rigid enough to support a supply bag; and
   wherein the middle portion supports the supply bag in a position suitable for therapy fluid to flow from the supply bag for a medical fluid treatment.

10. The medical fluid supply bag stand of claim 9, wherein the middle portion is flexible.

11. The medical fluid supply bag stand of claim 9, wherein the middle portion is configured to support the supply bag at an angle suitable to test whether the supply bag has been properly preset for the treatment.

12. The medical fluid supply bag stand of claim 9, wherein the middle portion is held at an angle suitable to cause a dual chamber supply bag to fold if a seal separating the dual chambers has not been opened or opened properly.

* * * * *